US012791538B2

(12) United States Patent
Meek et al.

(10) Patent No.: US 12,791,538 B2
(45) Date of Patent: Nov. 10, 2026

(54) DIAGNOSTIC SYSTEM FOR OXYGEN CONCENTRATORS

(71) Applicant: Oxus America, Inc., Auburn Hills, MI (US)

(72) Inventors: Sarah Meek, Rochester Hills, MI (US); Andrew Voto, Waterford, MI (US); Gary Abusamra, Rochester Hills, MI (US)

(73) Assignee: Oxus America, Inc., Auburn Hills, MI (US)

( * ) Notice: Subject to any disclaimer, the term of this patent is extended or adjusted under 35 U.S.C. 154(b) by 709 days.

(21) Appl. No.: 18/338,064

(22) Filed: Jun. 20, 2023

(65) Prior Publication Data

US 2023/0408468 A1 Dec. 21, 2023

Related U.S. Application Data

(60) Provisional application No. 63/354,121, filed on Jun. 21, 2022.

(51) Int. Cl.

*G01N 31/22* (2006.01)
*A61M 16/00* (2006.01)
*A61M 16/10* (2006.01)
*A61M 16/20* (2006.01)

(52) U.S. Cl.

CPC ....... *G01N 31/225* (2013.01); *A61M 16/0003* (2014.02); *A61M 16/10* (2013.01); *A61M 16/20* (2013.01); *A61M 2016/1025* (2013.01)

(58) Field of Classification Search

CPC . G01N 31/225; A61M 16/0003; A61M 16/10; A61M 16/20; A61M 2016/1025; B01D 53/047; B01D 53/0476; B01D 2253/108; B01D 2256/12; B01D 2257/102; B01D 2258/06; B01D 2259/40007; B01D 2259/40009; B01D 53/0454; Y10T 436/20; Y10T 436/207497; Y10T 436/25875

USPC ........................... 436/127, 136, 181; 422/83

See application file for complete search history.

(56) References Cited

U.S. PATENT DOCUMENTS

| | | | | |
|---|---|---|---|---|
| 4,627,860 | A * | 12/1986 | Rowland | A61M 16/101 128/204.22 |
| 7,017,386 | B2 | 3/2006 | Liu et al. | |
| 7,708,802 | B1 * | 5/2010 | Deane | B01D 53/047 96/417 |
| 8,888,902 | B2 | 11/2014 | Galbraith et al. | |
| 8,900,353 | B2 * | 12/2014 | Thompson | A61M 16/10 128/204.22 |
| 9,717,876 | B2 | 8/2017 | Wilkinson et al. | |
| 10,255,647 | B2 | 4/2019 | Rodman et al. | |
| 2006/0174877 | A1 | 8/2006 | Jagger et al. | |
| 2007/0227360 | A1 | 10/2007 | Atlas et al. | |
| 2009/0214393 | A1 * | 8/2009 | Chekal | C01B 13/0259 128/204.26 |
| 2013/0269519 | A1 | 10/2013 | Taylor et al. | |
| 2017/0087326 | A1 * | 3/2017 | Wilkinson | A61M 16/0672 |
| 2022/0016571 | A1 | 1/2022 | Yehya | |
| 2022/0096780 | A1 | 3/2022 | Miaralipour et al. | |

OTHER PUBLICATIONS

European Search Report for European Patent Application No. EP23180687.8 dated Nov. 3, 2023, 7 pages.

* cited by examiner

*Primary Examiner* — Maureen Wallenhorst

(74) *Attorney, Agent, or Firm* — Young Basile Hanlon & MacFarlane, P.C.

(57) ABSTRACT

An aspect of the disclosure is a diagnostic system. The diagnostic system includes a communications interface, an output gas interface, one or more sensors, and a controller that is configured to execute a diagnostic procedure. The diagnostic procedure causes the controller to transmit one or more commands to the oxygen concentrator using the communications interface, to obtain the one or more gas property measurements from the one or more sensors during operation of the oxygen concentrator, and to determine a diagnostic result by comparing the one or more gas property measurements obtained from the one or more sensors during operation of the oxygen concentrator to a testing standard described by the diagnostic procedure. The diagnostic procedure also causes the controller to output information regarding the diagnostic result for display to a user.

20 Claims, 3 Drawing Sheets

DIAGNOSTIC SYSTEM FOR OXYGEN CONCENTRATORS

CROSS-REFERENCE TO RELATED APPLICATION(S)

This application claims the benefit of U.S. Patent Application No. 63/354,121, filed on Jun. 21, 2022, the content of which is hereby incorporated by reference in its entirety for all purposes.

TECHNICAL FIELD

This disclosure relates to diagnostic systems for oxygen concentrators.

BACKGROUND

Oxygen concentrator systems generate substantially pure (e.g., 82-96% pure) oxygen gas using ambient air as an input gas. Oxygen concentrator systems are commonly used for medical applications by patients who have a need for substantially pure oxygen. Oxygen concentrator systems include portable systems that can be carried by patients, and non-portable systems that are often used in a medical facility or in a residential setting.

Some known oxygen concentrator systems operate on a pressure swing adsorption or vacuum pressure swing adsorption cycle. In such systems, ambient air is pressurized in a sieve bed of an adsorbent material that adsorbs nitrogen (e.g. zeolite), and substantially pure oxygen is then released from the sieve bed while the nitrogen is retained by the adsorbent material. The nitrogen may then be purged from the adsorbent material.

SUMMARY

Disclosed herein are implementations of a diagnostic system for oxygen concentrators and diagnostic methods for oxygen concentrators.

One aspect of the disclosure is a diagnostic system that includes a communications interface that is configured for communications with an oxygen concentrator, a pneumatic interface that is configuration for pneumatic communication with the oxygen concentrator, and one or more sensors that are configured to obtain one or more gas property measurements from the oxygen concentrator using the pneumatic interface. The diagnostic system also includes a controller that is configured to analyze information obtained from the oxygen concentrator using the communications interface and the one or more gas property measurements to determine a diagnostic result.

In some implementations, the controller is configured to determine the diagnostic result by comparing at least one of the information obtained from the oxygen concentrator and the one or more gas property measurements to a standard described by a diagnostic procedure. The controller may be configured to output the diagnostic result for display to a user. The controller may be further configured to identify information describing a service procedure based on the diagnostic result and output the information describing the service procedure for display to a user.

Another aspect of the disclosure is a diagnostic system. The diagnostic system includes a communications interface that is configured for communications with an oxygen concentrator. The diagnostic system also includes an output gas interface that is configured for pneumatic communication with the oxygen concentrator in order to receive an output gas from the oxygen concentrator. The diagnostic system also includes one or more sensors that are configured to obtain one or more gas property measurements of the output gas that is received from the oxygen concentrator using the output gas interface. The diagnostic system also includes a controller that is configured to execute a diagnostic procedure. The diagnostic procedure causes the controller to transmit one or more commands to the oxygen concentrator using the communications interface, wherein the one or more commands are configured to cause operation of the oxygen concentrator. The diagnostic procedure also causes the controller to obtain the one or more gas property measurements from the one or more sensors during operation of the oxygen concentrator, and determine a diagnostic result by comparing the one or more gas property measurements obtained from the one or more sensors during operation of the oxygen concentrator to a testing standard described by the diagnostic procedure. The diagnostic procedure also causes the controller to output information regarding the diagnostic result for display to a user.

Another aspect of the disclosure is a diagnostic system. The diagnostic system includes a communications interface that is configured for communications with an oxygen concentrator. The diagnostic system also includes an input gas interface that is configured for pneumatic communication with the oxygen concentrator. The diagnostic system also includes a gas supply that is configured to supply an input gas to the oxygen concentrator using the input gas interface. The diagnostic system also includes a controller that is configured to execute a diagnostic procedure. The diagnostic procedure causes the controller to transmit one or more commands to the oxygen concentrator using the communications interface, supply the input gas to the oxygen concentrator, obtain the one or more gas property measurements during supply of the input gas to the oxygen concentrator, and determine a diagnostic result by comparing the one or more gas property measurements to a testing standard described by the diagnostic procedure. The controller is also configured to output information regarding the diagnostic result for display to a user.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

The disclosure herein relates to diagnostic systems that are configured to analyze operation of an oxygen concentrator and determine a condition of the oxygen concentrator. The diagnostic systems may identify corrective actions that can be taken in response to the condition of the oxygen concentrator, and output information that describes the condition of the oxygen concentrator and/or the corrective actions. The identified corrective actions may be performed by a user (e.g., a qualified technician) using the information that describes the condition of the oxygen concentrator and/or the corrective actions.

Figure 1:
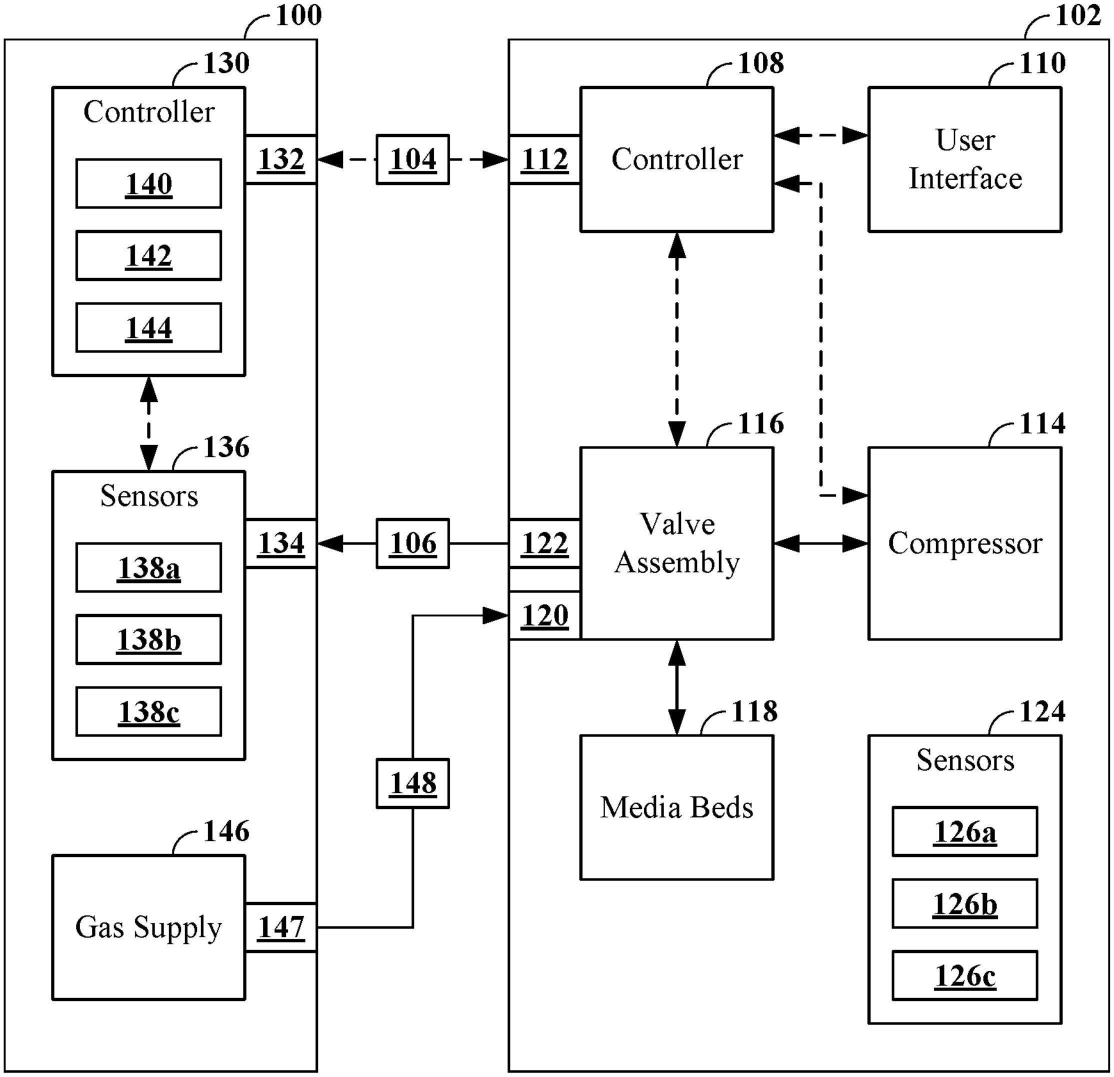
FIG. 1 is a block diagram that shows a diagnostic system and an oxygen concentrator.

FIG. 1 shows a diagnostic system 100 that is connected to an oxygen concentrator 102 according to an example. The diagnostic system 100 is connected to the oxygen concentrator 102 by a communications connection 104 and by an output gas connection 106. The communications connection 104 may be a data connection between the diagnostic system 100 and the oxygen concentrator 102. The communications connection 104 may allow transmission of signals and/or data between the diagnostic system 100 and the oxygen concentrator 102. The communications connection 104 may be a wired or wireless connection. The output gas connection 106 is a fluid (e.g., air or oxygen) carrying connection between the diagnostic system 100 and the oxygen concentrator 102, and establishes fluid communication between a portion of the diagnostic system 100 and a portion of the oxygen concentrator 102. The output gas connection 106 may be a single connection or multiple connections, and thus, the diagnostic system 100 may be connected to the oxygen concentrator 102 by one or more pneumatic connections. The diagnostic system 100 will be described in detail herein.

The oxygen concentrator 102 may be an oxygen concentration device of any kind, such as one that operates on a pressure swing adsorption (PSA) cycle or a vacuum pressure swing adsorption (VPSA) cycle. The oxygen concentrator 102 is operable to receive air as an input gas and separate the air into constituent components. In particular, the oxygen concentrator 102 can be operable to generate a product gas that is substantially pure oxygen. The substantially pure oxygen has a much higher oxygen concentration than ambient air. As an example, the substantially pure oxygen can be approximately 82-96% oxygen.

The oxygen concentrator 102 includes controller 108, a user interface 110, and a communications interface 112. The controller 108 is configured to regulate operation of the oxygen concentrator 102 and control operation of various components of the oxygen concentrator 102. In some implementations, the controller 108 may include a general purpose computing device, such as a computing device that includes one or more processors, a short term memory device, and a long term storage device. In some implementations, the controller 108 may include a special purpose computing device, such as an integrated circuit or an application-specific integrated circuit. The controller 108 may be provided with control software that is executed by the controller 108 to cause the controller 108 to cause operation of the various components of the oxygen concentrator 102 is a desired manner. The user interface 110 may include components such as buttons, knobs, and other types of input components that allow a user to change the operating state of the oxygen concentrator 102, such as by starting and stopping production of the product gas. The user interface 110 may include output components that show information regarding the system of the oxygen concentrator 102. The communications interface 112 is a hardware component that is configured to facilitate communication with the diagnostic system 100, such as a wired communications device and/or a wireless communications device.

To implement a VPSA or PSA cycle, the oxygen concentrator 102 may include a compressor 114, a valve assembly 116, and media beds 118. The media beds 118 include an adsorbent material that is used to separate oxygen from other components of ambient air, such as nitrogen. In some implementations, the adsorbent material is a zeolite material.

The oxygen concentrator 102 includes an inlet port 120 (e.g., an ambient air inlet port) and an outlet port 122 (e.g., a product gas outlet port), which may both connected to the valve assembly 116 to allow individual valves of the valve assembly 116 to regulate flow of gas into and out of the oxygen concentrator 102. During normal operation of the oxygen concentrator 102 inlet port 120 is exposed to ambient air from the environment around the oxygen concentrator 102. During normal operation of the oxygen concentrator 102, the outlet port 122 is configured to deliver the product gas for use in an intended application, such as by supplying the product gas to a cannula for administration to a person.

To produce the product gas (e.g., substantially pure oxygen), air from the inlet port 120 is supplied to the compressor 114 by operation of the valve assembly 116 and is supplied to the media beds 118 at a pressure that is higher than ambient pressure. The air is subsequently released from the media beds 118 as the product gas. In particular, after the media beds 118 are pressurized, the valve assembly 116 is operated to establish fluid communication between the media beds 118 and the outlet port 122, in order to supply the product gas to the outlet port 122 for use.

The pressure at which the air is supplied to the media beds 118 is selected based on the material properties of the adsorbent material in the media beds 118. In particular, adsorption is dependent on pressure, and the volume of a gas that is adsorbed by the adsorbent material increases as the pressure rises. In addition, nitrogen is adsorbed by the adsorbent material that is used in the media beds 118 (e.g., zeolite) more readily than oxygen is at the same pressure. Thus, pressurization of the media beds 118 causes adsorption of a portion of the nitrogen in the air supplied to the media beds 118. As needed, the media beds 118 can be purged by lowering the pressure in the media beds 118 so that the nitrogen is released from the adsorbent material, and this gas is vented from the oxygen concentrator 102.

To allow the controller 108 to regulate operation of the oxygen concentrator 102, the oxygen concentrator 102 includes one or more sensors 124. The one or more sensors 124 may each be electrically connected to the controller 108 to allow the one or more sensors 124 to transmit sensor output signals to the controller 108, where the sensor output signals represent measurements of gas properties by the one or more sensors 124. As an example, some or all of the one or more sensors 124 may be configured to measure one or more properties of the gas within the oxygen concentrator 102. These sensors may be located at various locations (e.g., along various flow paths, such as conduits that carry gas) within the oxygen concentrator 102. As examples, the one or more sensors 124 may include sensors located at the inlet port 120 at the outlet port 122, upstream or downstream of the compressor 114, upstream or downstream of the media beds 118, and/or at other locations within the oxygen concentrator 102.

The one or more sensors 124 of the oxygen concentrator 102 are operable to measure properties of the gas that is flowing through the oxygen concentrator 102, such as flow rate, oxygen concentration, and pressure. The one or more sensors 124 may include, as examples, a flow meter **126*a*, an oxygen sensor 126*b*, and a pressure transducer 126*c*. The flow meter 126*a* is configured to measure a flow rate of gas at a location within the oxygen concentrator 102, such as along a flow path that is in communication with one of the inlet port 120 or the outlet port 122. The oxygen sensor 126*b*** is configured to measure a proportion of oxygen that is present in gas at a location within the oxygen concentrator 102, such as downstream from the media beds 118 or along a flow path that is in communication with the outlet port 122. As an example the proportion of oxygen present may be expressed as a percentage, in order to allow the oxygen concentrator 102 to determine the amount of oxygen that is contained in the product gas that is being supplied by the oxygen concentrator 102 at the outlet port 122. The pressure transducer 126*c* is configured to measure a pressure of gas within the oxygen concentrator 102. As an example, the pressure transducer 126*c* may be located along a flow path that is downstream of the compressor 114 and/or in communication with the media beds 118 to allow the controller to regulate pressurization of the media beds 118 by operation of the compressor 114.

The diagnostic system 100 includes a controller 130, a communications interface 132, an output gas interface 134 (e.g., a pneumatic interface configured to receive the output gas), and one or more sensors 136.

The controller 130 is configured to regulate operation of the diagnostic system 100 and control operation of various components of the diagnostic system 100. In some implementations, the controller 130 may include a general purpose computing device, such as a computing device that includes one or more processors, a short term memory device, and a long term storage device. In some implementations, the diagnostic system 100 may include a special purpose computing device, such as an integrated circuit or an application-specific integrated circuit. The diagnostic system 100 may be provided with control software that is executed by the diagnostic system 100 to cause the controller 108 to cause operation of the various components of the oxygen concentrator 102 in a desired manner. It should be understood that the controller 130 may be implemented using one or more computing devices. For example, some features of the diagnostic system, such as the communications interface 132, the output gas interface 134, and the one or more sensors 136 may be located in a housing, and some or all of the functions described with respect to the controller 130 may be implemented using an external computing device which may be, as examples, a desktop computer, a laptop computer, a tablet computer, or a smart phone.

The communications interface 132 is a hardware component that is configured to facilitate communication with the oxygen concentrator 102, such as a wired communications device and/or a wireless communications device. The communications interface 132 of the diagnostic system 100 is connectable to and disconnectable from the communications interface 112 of the oxygen concentrator 102 by the communications connection 104. The communications interface may receive information from sensors that are incorporated in the oxygen concentrator 102, and this information can be used for diagnostic purposes. As an example, sensors associated with the oxygen concentrator 102 may measure the output of the compressor 114 of the oxygen concentrator 102, including measurement of flow rate and pressure at the output of the compressor 114.

The output gas interface 134 includes an inlet (or multiple inlets, e.g., one or more inlets) for receiving an output gas, such as the product gas, from the oxygen concentrator 102. The output gas interface 134 is connectable to and disconnectable from the oxygen concentrator 102 by the output gas connection 106, such as by connection of the output gas interface 134 to the outlet port 122 of the oxygen concentrator 102 by the output gas connection 106. Alternatively, the output gas connection 106 may be coupled to a separate outlet port of the oxygen concentrator 102 that is used for diagnostic procedures. One or more such dedicated outlet ports may be provided, and may allow the output gas from the oxygen concentrator 102 to pass out of the oxygen concentrator 102 without passing through one or more of the components that the gas would pass through during normal operation, thereby allowing components of the oxygen concentrator 102 to be tested independently relative to one or more upstream or downstream components. As will be explained further herein, isolating components in this manner allows for more accurate diagnosis of faults of the oxygen concentrator 102.

The one or more sensors 136 are operable to measure properties of the gas received by the diagnostic system 100 using the output gas interface 134, such as flow rate, oxygen concentration, and pressure. The one or more sensors 136 may include, as examples, a flow meter 138*a*, an oxygen sensor 138*b*, and a pressure transducer 138*c*. The flow meter 138*a* is configured to measure a flow rate of the product gas that is received by the diagnostic system 100 from the oxygen concentrator 102 at the output gas interface 134 and allows the diagnostic system 100 to measure the amount of the product gas that is being produced by the oxygen concentrator 102. The oxygen sensor 138*b* is configured to measure a proportion of oxygen that is present in the product gas, which may be expressed as a percentage, in order to allow the diagnostic system 100 to determine the amount of oxygen that is contained in the product gas that is produced by the oxygen concentrator 102. The pressure transducer 138*c* is configured to measure a pressure of the product gas that is that being produced by the oxygen concentrator 102.

The diagnostic system 100 can be connected to the oxygen concentrator 102 by the communications connection 104 and/or the output gas connection 106 to allow the diagnostic system 100 to perform diagnostic functions. As an example, the oxygen concentrator 102 may be configured to transmit data to the diagnostic system 100 using the communications connection 104. The data that is transmitted from the oxygen concentrator 102 to the diagnostic system 100 may include usage history information, such as a total number of hours of operation of the oxygen concentrator 102, a number of hours of operation of the oxygen concentrator 102 since it was last serviced, and/or a number of hours of operation of the oxygen concentrator 102 since the media beds 118 were last replaced. The data that is transmitted from the oxygen concentrator 102 to the diagnostic system 100 may include data that indicates a particular error state, such as a code that corresponds to an error condition. The data that is transmitted from the oxygen concentrator 102 to the diagnostic system 100 may include data that represents current operating states of the oxygen concentrator 102, data that represents historical operating states of the oxygen concentrator 102 (e.g., a stored operating state data log), data that represents current output values from one or more sensors of the oxygen concentrator 102, and data that represents historical output values from one or more sensors of the oxygen concentrator 102 (e.g., a stored sensor data log).

As another example, the diagnostic system 100 may be configured to transmit a request to the oxygen concentrator 102 using the communications connection 104. The request may, for example, specify information to be transmitted to the diagnostic system 100 from the oxygen concentrator 102.

As another example, the diagnostic system 100 may be configured to transmit a command to the oxygen concentrator 102. Examples of commands that may be transmitted to the oxygen concentrator 102 by the diagnostic system 100 include commands that cause the oxygen concentrator 102 to start or stop operation of a component (e.g., to turn on a motor of the compressor 114, to change the position of a valve from the valve assembly 116 between open and closed, to change an opening degree of a proportional valve from the valve assembly 116, etc.), to adjust a setting that affects operation of the oxygen concentrator 102, or to otherwise control operation of the oxygen concentrator 102 or a component of the oxygen concentrator 102. A command sent to the oxygen concentrator 102 by the diagnostic system 100 may cause the oxygen concentrator 102 to perform a diagnostic routine (e.g., a diagnostic routine that was previously stored by a controller of the oxygen concentrator 102) that includes performing a sequence of operations that are intended to allow testing of a function of the oxygen concentrator 102. A command sent to the oxygen concentrator 102 may include information that defines a diagnostic routine (e.g., in the form of a script, a series of commands, etc.) and the causes the oxygen concentrator 102 to perform the operations of the diagnostic routine.

The diagnostic system 100 may include a data store 140 that is accessible to the controller 130. As examples, the data store 140 may be a data file that is stored on a storage device that is associated with the controller, or the data store 140 may be a data file that is stored by a remote system and is accessible to the diagnostic system 100 using a wired or wireless communications network. The data store 140 is configured to store information about the oxygen concentrator 102, as well as information about other oxygen concentrators that are analyzed by the diagnostic system 100. The data store 140 may store information describing the oxygen concentrator 102, information regarding previous maintenance tasks that were performed on the oxygen concentrator 102, results from previous diagnostic tests that were performed on the oxygen concentrator 102, and/or other information regarding the oxygen concentrator 102.

The diagnostic system 100 includes diagnostic procedures 142 that are accessible to the controller 130. As examples, the diagnostic procedures 142 may be or include computer program instructions that are executable by the controller 130 of the diagnostic system 100 and that, when executed, cause the controller 130 to perform operations that correspond to one or more diagnostic tests that are intended to assess the operating condition of the oxygen concentrator 102, identify potential problems that may need to be corrected, and output information describing results of the diagnostic test and suggested remedial actions. The diagnostic procedures may be or include computer program instructions and/or additional information that stored on a storage device that is associated with the controller, or the diagnostic procedures 142 may be or include computer program instructions and/or additional information that is stored by a remote system and is accessible to the diagnostic system 100 using a wired or wireless communications network.

The diagnostic procedures 142 are used by the controller 130 to diagnose a condition of the oxygen concentrator 102. As an example, the controller 130 may be configured to analyze information obtained from the oxygen concentrator 102 using the communications connection 104 and to analyze one or more gas property measurements that are recorded by the one or more sensors 136 to determine a diagnostic result. As one example, the controller 130 may be configured to determine the diagnostic result by comparing the information obtained from the oxygen concentrator 102 to a testing standard described by a diagnostic procedure from the diagnostic procedures 142. As another example, the controller 130 may be configured to determine the diagnostic result by comparing the one or more gas property measurements to a testing standard described by a diagnostic procedure from the diagnostic procedures 142. Once the diagnostic result has been determined, the diagnostic result may be reported to a user, such as a service technician. As an example, the controller 130 may be configured to output the diagnostic result for display to a user, using a display device or other means of output.

The diagnostic system 100 includes service procedure descriptions 144 that are accessible to the controller 130. The service procedure descriptions 144 may be in the form of information stored on a storage device that is associated with the controller 130, or in the form of information that is stored by a remote system and is accessible to the diagnostic system 100 using a wired or wireless communications network. As examples, the service procedure descriptions 144 may be or include information that describes service procedures that can be performed in response to a particular diagnostic result. As an example, each of the service procedure descriptions 144 may be related to one or more diagnostic results so that a description of a relevant service procedure may be output for display to a user in response to determination of a particular diagnostic result. In response to determination of the diagnostic result, the controller 130 may identify one of the service procedure descriptions 144 that corresponds to the diagnostic result. For example, the controller 130 may be configured to identify information describing a service procedure from the service procedure descriptions 144 based on the diagnostic result and output the information describing the service procedure for display to a user, for example, using a display device or other means of output.

Diagnostic procedures may be performed using ambient air as an input gas for the oxygen concentrator, where the ambient air is introduced in to the oxygen concentrator 102 from the ambient environment at the inlet port 120. However, to implement some diagnostic procedures, an input gas may be supplied to the oxygen concentrator 102 from a gas supply 146 that is included in the diagnostic system 100 or associated with the diagnostic system 100. As an example, the diagnostic system may regulate supply of the input gas to the oxygen concentrator 102 from the gas supply 146 according to the needs of a particular diagnostic procedure. In the illustrated example, the gas supply 146 is incorporated in the diagnostic system 100 and is pneumatically coupled to an input gas interface 147 (e.g., a pneumatic interface configured to supply the input gas) that may be configured in the same manner as the output gas interface 134. An input gas connection 148 is implemented in the same manner as the output gas connection 106 and serves to transmit an input gas from the gas supply 146, via the input gas interface 147, to the oxygen concentrator 102, for example, to the inlet port 120 thereof.

It should be understood that, during a diagnostic procedure, gas from the gas supply may be provided to the oxygen concentrator 102 through a port other than one used for typical operation, such as through a separate port that is dedicated to diagnostic usage. Such a port may allow routing of the gas from the gas supply 146 in a way that differs from normal flow of gas through the oxygen concentrator 102, for example, to allow isolated testing of a particular component of the oxygen concentrator 102. Furthermore, it should be understood that multiple such ports may be provided, for example, to allow for isolated testing of multiple different components. As an alternative, isolated testing may be implemented by controlling flow of gas through the oxygen concentrator using the valve assembly 116, as will be described further herein.

Figure 2:
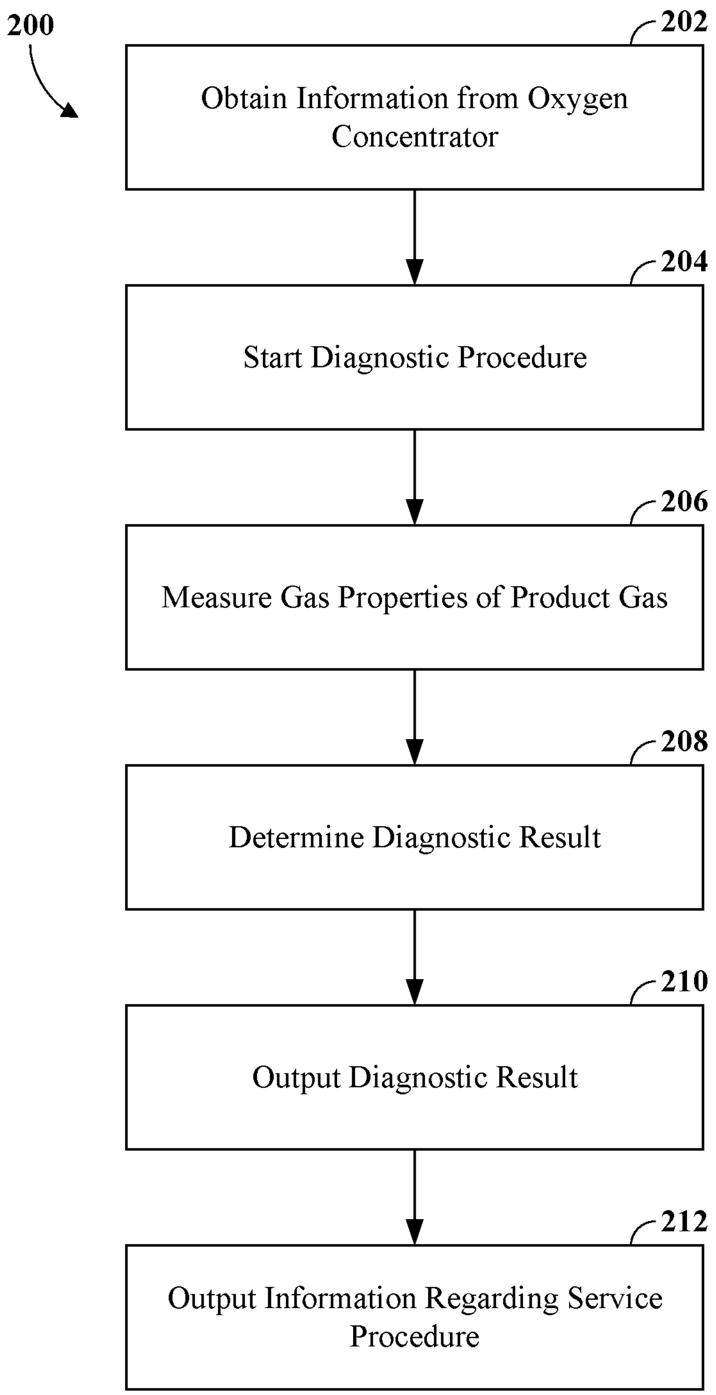
FIG. 2 is a flowchart that shows a diagnostic process.

FIG. 2 is an illustration that shows an example of a diagnostic process 200. The diagnostic process 200 may be implemented partly or wholly in the form of computer program instructions that are executable by a computing device, and, when executed, cause a system to perform operations that correspond to the operations of the diagnostic process 200 as will be described further herein. In some implementations, the computer program instructions that implement the diagnostic process 200 may be stored by a memory device and executed by a processor that obtains the computer program instructions from the memory device. In some implementations, the computer program instructions that implement the diagnostic process 200 may be embodied in the form of a non-transitory computer readable storage device that contains the computer program instructions.

Before the diagnostic process 200 begins, the diagnostic system 100 is connected to the oxygen concentrator 102, for example, by the communications connection 104 and the output gas connection 106. In operation 202, information is obtained from the oxygen concentrator 102 by the diagnostic system 100. As examples, the information may describe operating states of components of the oxygen concentrator 102, measurements from sensors of the oxygen concentrator 102, and/or other conditions. Obtaining information from the oxygen concentrator 102 may be performed continuously during further steps of the diagnostic process 200.

In operation 204, a diagnostic procedure is started. As an example the diagnostic procedure can be started by sending one or more commands from the diagnostic system 100 to the oxygen concentrator 102 using the communications connection 104. The commands may, for example, cause the oxygen concentrator 102 to start producing product gas, and may specify parameters for production of the product gas, such as a commanded flow rate for the product gas or a commanded output pressure for the product gas. During production of the product gas by the oxygen concentrator 102, the product gas flows from the oxygen concentrator 102 to the diagnostic system 100 over the output gas connection 106.

In operation 206, one or more gas properties of the product gas are measured, such as flow rate, oxygen concentration, and pressure. These measurements may be made, for example, by the sensors 124 of the oxygen concentrator 102 or the sensors 136 of the diagnostic system 100. Other information may be obtained from the oxygen concentrator 102 and used for diagnostic purposes, such as information output by the controller 108 of the oxygen concentrator 102.

In operation 208, the information obtained from the oxygen concentrator 102 in operation 202 and/or the one or more gas property measurements obtained in operation 206 are analyzed to determine a diagnostic result. This analysis may be performed using the information from the data store 140 As one example, the gas property measurements may be compared to standards including stored measurements that are indicative of acceptable operation of the oxygen concentrator 102, unacceptable operation of the oxygen concentrator 102, a particular fault in one of the components of the oxygen concentrator 102, or another diagnosable circumstance. As an example, deviation of single measurement from a standard by a predetermined amount may be associated with a fault of a particular component. As another example, such as deviation may be associated with several different potential faults, and deviations of other measurements may be used to further understand which fault may be presented in the oxygen concentrator 102 (e.g., some faults may be associated with deviations of two or more different measurements from respective standards).

In operation 210, information describing the diagnostic result is output for display to the user. This information may include a fault identified by the analysis of operation 208, and may identify a faulty component. In operation 212, information describing a service procedure is identified based on the diagnostic result and is output for display to the user. This information may be identified by the type of fault or identity of the faulty component. As an example, the type of fault of faulty component may be used as database search terms to identify one or more of the service procedure descriptions 144 as corresponding to the fault identified in the diagnostic result.

Information from the diagnostic process 200 can be used to refine the diagnostic procedure. As an example, the result of the diagnostic procedure can be used to modify the algorithm or model used to implement the diagnostic procedure to improve efficiency of the diagnostic result of operation 210 and service procedure that is identified in operation 212, such as by determining a relationship between an observed condition (e.g., a failure of the system or parameters falling outside acceptable ranges) and root causes, so that potential root causes can be ranked according to the likelihood that they are associated with the state of the oxygen concentrator 102 that is being analyzed. This allows common root causes to be identified and investigated first. As another example, the information collected during the diagnostic process 200 may be used build a training data set for a machine learning model, by setting measurements and/or other observed circumstances as inputs, and identification of the fault as an output. During training, the identity of the fault may be used as a ground truth value for comparison with the output of the model, and for determination of an error value that is used to further train the model by backpropagation. The trained model may be then used in the diagnostic process to determine faults in the oxygen concentrator based on gas property measurements and/or other data determined by the diagnostic system.

In some implementations, normal operation of an oxygen concentrator may be modified in order to facilitate testing by the diagnostic system 100. The following examples describe such modifications using the oxygen concentrator 102 as an example, but it should be understood that these techniques may be applied to oxygen concentrators of various configurations.

Figure 3A:
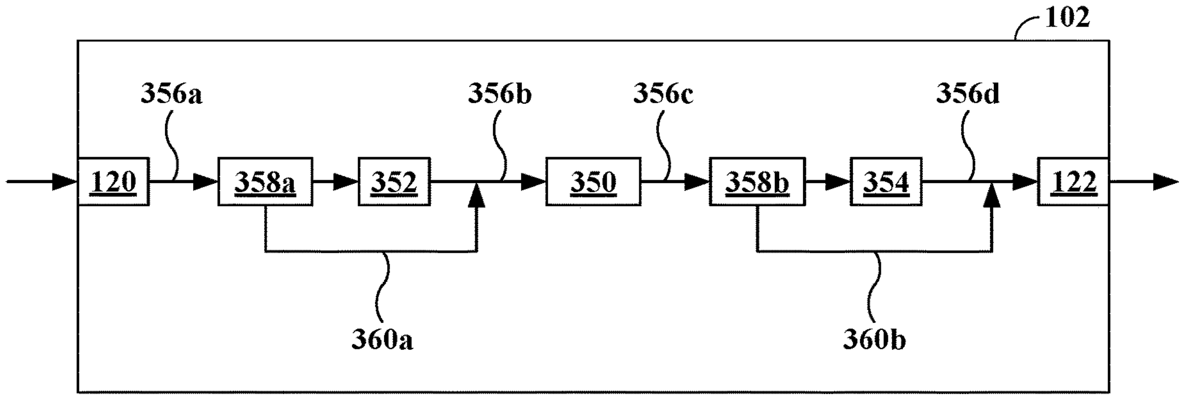
FIG. 3A is a schematic illustration of an example configuration of the oxygen concentrator that is used to perform a diagnostic procedure.

FIG. 3A is a schematic illustration in which a diagnostic procedure is being performed by the diagnostic system 100 to test functionality of the oxygen concentrator 102. Some components of the oxygen concentrator 102 are represented in FIG. 3A by a subject component 350, upstream components 352, and downstream components 354.

The subject component 350 represents a component of the oxygen concentrator 102 that is being evaluated during the diagnostic procedure. As examples, the subject component 350 may be one of the compressor 114, the valve assembly 116, the media beds 118, or one of the sensors 124.

The upstream components 352 represent one or more components of the oxygen concentrator 102 that are positioned between the inlet port 120 and the subject component 350. The downstream components 354 represent one or more components of the oxygen concentrator 102 that are positioned between the subject component 350 and the outlet port 122. The downstream components 352 and the upstream components 354 may each be or include one or more components of the oxygen concentrator 102, such as one or more of the compressor 114, the valve assembly 116, the media beds 118, and/or one or more of the sensors 124.

In the illustrated implementation, a first flow path 356*a* extends from the inlet port 120 to the downstream components, and a second flow path 356*b* extends from the downstream components 352 to the subject component 350. A third flow path 356*c* extends from the subject component 350 to the downstream components 354, and a fourth flow path 356*d* extends from the downstream components 354 to the outlet port 122.

During normal operation of the oxygen concentrator 102 to produce the product gas, for example, according to the PSA cycle or the VPSA cycle, gas travels through the oxygen concentrator 102 from the inlet port 120 to the outlet port 122 in a predetermined manner that implements the cycle being used to produce the product gas. As an example, an input gas, such as ambient air, may enter the inlet port 120, flow to the upstream components via the first flow path 356*a*, flow from the upstream components to the subject component 350 via the second flow path 356*b*, flow from the subject component 350 to the downstream components 354 via the third flow path 356*c*, and flow from the downstream components 354 to the outlet port 122 via the fourth flow path 356*d*. During flow through the oxygen concentrator 102 under normal operation, the input gas is processed by components of the oxygen concentrator 102 as previously described to produce the product gas as desired.

The diagnostic procedure may include operation of components of the oxygen concentrator 102 in a manner that does not result in a specific product gas (e.g., substantially pure oxygen). Instead, during the diagnostic procedure, the flow of gas through the oxygen concentrator 102 may be modified to allow for diagnosis of a fault in one or more of the components of the oxygen concentrator 102.

As an example, the flow of gas through the oxygen concentrator 102 may be modified to bypass some or all of the components of the oxygen concentrator 102, such as the downstream components 352 and/or the upstream components 354. By modifying the flow of gas through the oxygen concentrator 102, the subject component 350 may be tested in isolation from other components. This may be advantageous during some diagnostic activities, as a particular issue (e.g., low oxygen concentration, flow rate, low pressure, etc.) may have multiple potential route cause. By testing only a single component or a limited group of components (e.g., by excluding one or more components involved in normal operation of the oxygen concentrator) excluded components are eliminated as a potential source of any issues observed during diagnostic testing, and multiple diagnostic tests may be performed to evaluate various components of the oxygen concentrator 102.

In the illustrated implementation, the oxygen concentrator 102 includes a first bypass valve 358*a*, a first bypass path 360*a*, a second bypass valve 358*b*, and a second bypass path 360*b*, which may be used during diagnostic procedures. The first bypass valve 358*a* and the second bypass valve 358*b* may be valves that are included in the valve assembly 116, and the description of the valve assembly 116 is therefore applicable to them. The first bypass valve 358*a* and the second bypass valve 358*b* may be controlled by the controller 108 of the oxygen concentrator 102, by the controller 130 of the diagnostic system 100, and/or by the controller 108 of the oxygen concentrator 102 in response to a command received by the oxygen concentrator 102 from the diagnostic system 100.

The first bypass valve 358*a* and the first bypass path 360*a* are configured to allow a flow of gas through the oxygen concentrator 102 to bypass the upstream components 352. The first bypass path 360*a* is not used during normal operation of the oxygen concentrator 102, and instead is configured to facilitate diagnostic procedures.

The first bypass valve 358*a* is located along the first flow path 356*a* and is connected to the first bypass path 360*a*, which extends from the first flow path 356*a* to the second flow path 356*b*. The first bypass valve 358*a* is configured redirect the flow of the gas so that it flows to the subject component 350 via the first bypass path 360*a* and the second flow path 356*b* without first flowing through the upstream components 352. Thus, when the first bypass valve 358*a* in a first position (e.g., a normal operating position), it directs the gas to the upstream components 352, and when the first bypass valve 358*a* is in a second position (e.g., a diagnostic testing position), it causes the gas to bypass the upstream components 352 and the gas is instead shunted to the subject component 350 along the first bypass path 360*a*.

The second bypass valve 358*b* and the second bypass path 360*b* are configured to allow a flow of gas through the oxygen concentrator 102 to bypass the downstream components 354. The second bypass valve 358*b* is located along the third flow path 356*c* and is connected to the second bypass path 360*b*, which extends from the third flow path 356*c* to the fourth flow path 356*d*. The second bypass valve 358*b* is configured redirect the flow of the gas so that it flows to the outlet port 122 via the second bypass path 360*b* and the fourth flow path 356*d* without first flowing through the downstream components 354. Thus, when the second bypass valve 358*b* in a first position (e.g., a normal operating position), it directs the gas to the downstream components 354, and when the second bypass valve 358*b* is in a second position (e.g., a diagnostic testing position), it causes the gas to bypass the downstream components 354 and the gas is instead shunted to the outlet port 122 along the second bypass path 360*b*.

Figure 3B:
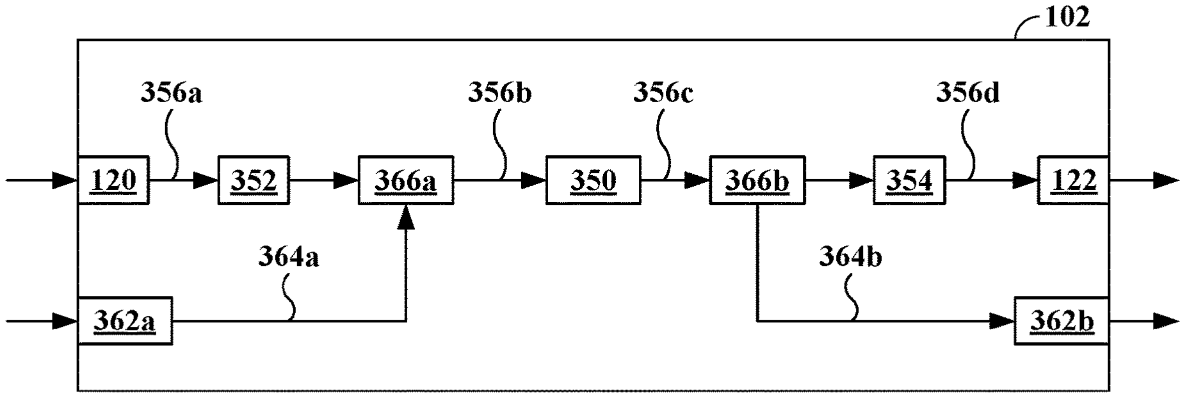
FIG. 3B is a schematic illustration of an example configuration of the oxygen concentrator that is used to perform a diagnostic procedure.

FIG. 3B is a variation of the implementation shown in FIG. 3A. Flow through the oxygen concentrator 102 during normal operation is the same as previously described. In this implementation, the first bypass valve 358*a*, the first bypass path 360*a*, the second bypass valve 358*b*, and the second bypass path 360*b* are omitted. Instead, the oxygen concentrator 102 includes a diagnostic inlet port 362*a*, a diagnostic inlet path 364*a*, a diagnostic inlet valve 366*a*, a diagnostic outlet port 362*b*, a diagnostic outlet path 364*b*, and a diagnostic outlet valve 366*b*. These components are configured to allow the subject component 350 to be analyzed in isolation from the upstream components 352 and the downstream components 354. The diagnostic inlet port 362*a*, the diagnostic inlet path 364*a*, the diagnostic outlet port 362*b*, and the diagnostic outlet path 364*b* are not used during normal operation of the oxygen concentrator 103. The diagnostic inlet valve 366*a* and the diagnostic outlet valve 366*b* may be valves that are included in the valve assembly 116, and the description of the valve assembly 116 is therefore applicable to them. The diagnostic inlet valve 366*a* and the diagnostic outlet valve 366*b* may be controlled by the controller 108 of the oxygen concentrator 102, by the controller 130 of the diagnostic system 100, and/or by the controller 108 of the oxygen concentrator 102 in response to a command received by the oxygen concentrator 102 from the diagnostic system 100.

Flow through the oxygen concentrator 102 is normal when the diagnostic inlet valve 366*a* and the diagnostic outlet valve 366*b* are each in a first position (e.g., a normal operating position), and gas flows between the inlet port 120 and the outlet port 122 through the upstream component 352, the subject component 350, and the downstream component 354. With the diagnostic inlet valve 366*a* and the diagnostic outlet valve 366*b* each in a second position (e.g., a diagnostic testing position), gas may be supplied to the diagnostic inlet valve 366*a* and may exit at the diagnostic outlet valve 366*b*. This allows the gas to flow from the diagnostic inlet valve 366*a* to the subject component 350 via the diagnostic inlet path 364*a*, and to flow from the subject component 350 to the diagnostic outlet valve 366*b* via the diagnostic outlet path 364*b*. In this way, the upstream component 352 and the downstream component 354 are bypassed, such that the gas supplied at the diagnostic inlet valve 366*a* does not flow through the upstream component 352 or the downstream component 354.

While the configurations of FIGS. 3A and 3B are shown and described separately, it should be understood that features from these two configurations may be combined. As an example, a diagnostic path may be used to isolate the subject component 350 from one or more other components of the oxygen concentrator 102, while a bypass path may be used to isolate the subject component 350 from one or more other components of the oxygen concentrator 102.

In an example of a diagnostic procedure that includes analysis of functionality of the compressor 114, the oxygen concentrator 102 is configured as shown in FIG. 3A, and the subject component 350 represents the compressor 114. During the diagnostic procedure, for example, in operation 204 of the diagnostic process 200, the diagnostic system 100 sends a command to the oxygen concentrator 102 via the communications connection 104 to cause the first bypass valve 358*a* and/or the second bypass valve 358*b* to move to their respective second positions (e.g., diagnostic positions). This command may be sent in order to bypass the upstream components 352 and/or the downstream components 354, thereby allowing the gas to flow to the compressor 114 directly, so that operation of the compressor 114 may be evaluated in isolation from the upstream components 352 and/or the downstream components 354. As one example, the compressor 114 may be isolated from one or more of the valves from the valve assembly 116. As another example, the compressor 114 may be isolated from the media beds 118.

While isolated from one or more of the other components of the oxygen concentrator 102, the compressor 114 is then operated to compress gas that is received at the inlet port 120, and to supply the compressed gas to the outlet port. The compressor 114 may be activated in response to a command transmitted from the controller 130 of the diagnostic system 100 to the controller 108 of the oxygen concentrator 102. In this implementation, during operation of the compressor 114, ambient air enters the oxygen concentrator 102 at the inlet port 120, is provided to the compressor 114, and then flows to the outlet port 122. The outlet port 122 may be connected to the diagnostic system 100 by the output gas connection 106, such that one or more gas properties of the gas output by the compressor 114 may be measured by the sensors 136 of the diagnostic system 100. As one example, the flow rate of the gas output by the compressor 114 may be measured by the flow meter 138*a* of the diagnostic system 100. As another example, the pressure of the gas output by the compressor 114 may be measured by the pressure transducer 138*c* of the diagnostic system 100. Alternatively, the gas properties of the gas output by the compressor 114 may be analyzed by the sensors 124 of the oxygen concentrator 102, such as the flow meter 126*a* and/or the pressure transducer 126*c*, and the sensor output signals or values derived therefrom may be transmitted to the controller 130 of the diagnostic system 100 via the communications connection 104.

In an alternative implementation of the above diagnostic procedure for analyzing functionality of the compressor 114, the oxygen concentrator 102 is configured as shown in FIG. 3B. The diagnostic procedure for the compressor 114 is implemented in accordance with the previous description, except that gas (e.g., ambient air) enters via the diagnostic inlet port 362*a* and is directed to the subject component 350 (e.g., the compressor 114 in this example) using the diagnostic inlet path 364*a* and the diagnostic inlet valve 366*a*, flows to the compressor 114 where it is compressed, and then flows to the diagnostic outlet port 362*b* using the diagnostic outlet path 364*b* and the diagnostic outlet valve 366*b*. In this implementation, the output gas connection 106 is coupled to the diagnostic outlet port 362*b* and supplies the gas output by the compressor 114 to the diagnostic system 100 for analysis, such as by the sensors 136 thereof, as previously described.

In an example of a diagnostic procedure that includes analysis of functionality of the media beds 118, the oxygen concentrator 102 is configured as shown in FIG. 3A, and the subject component 350 represents the media beds 118. During the diagnostic procedure, for example, in operation 204 of the diagnostic process 200, the diagnostic system 100 sends a command to the oxygen concentrator 102 via the communications connection 104 to cause the first bypass valve 358*a* and/or the second bypass valve 358*b* to move to their respective second positions (e.g., diagnostic positions). This command may be sent in order to bypass the upstream components 352 and/or the downstream components 354, thereby allowing the gas to flow to the compressor 114 directly, so that operation of the media beds 118 may be evaluated in isolation from the upstream components 352 and/or the downstream components 354. As one example, the media beds may be isolated from one or more of the valves from the valve assembly 116. As another example, the media beds 118 may be isolated from the compressor 114. This allows a potential fault of the media beds 118 to be diagnosed in isolation from a potential fault of one or more other components of the oxygen concentrator, such as a fault of the valve assembly 116 or a fault of the compressor 114.

While isolated from one or more of the other components of the oxygen concentrator 102, gas is supplied to the media beds 118 in a manner that is suitable to generate a desired product gas (e.g., substantially pure oxygen) using the media beds 118. In this implementation, the media beds 118 may be isolated from the compressor 114, such that the compressor 114 of the oxygen concentrator 102 is not used during this diagnostic procedure. Instead, gas is supplied to the media beds 118 at necessary pressures according to a particular operating cycle (e.g., the PSA cycle or the VPSA cycle) by the gas supply 146 of the diagnostic system 100 via the input gas connection 148. In this implementation, the gas supply 146 of the diagnostic system may include a compressor that is equivalent to the compressor 114, in order to intake ambient air and compress it for supply to the media beds 118 of the oxygen concentrator 102 at a desired pressure.

Subsequent to supply of compressed gas to the media beds 118 by the gas supply 146, sensors are used to measure properties of the product gas output by the media beds 118. As examples, the flow rate, oxygen content, and pressure of the product gas may be measured, and these values may be compared to expected values by the diagnostic system 100 as previously described. These measurements may be performed using the sensors 124 of the oxygen concentrator 102, such as the flow meter 126*a*, the oxygen sensor 126*b*, and the pressure transducer 126*c*, and the measurements may then be transmitted to the diagnostic system 100 for analysis using the communications connection 104. Alternatively, by supplying the product gas to the diagnostic system 100 using the output gas connection 106, the properties of the product gas may be measured using the sensors 136 of the diagnostic system 100, such as the flow meter 126*a*, the oxygen sensor 126*b*, and the pressure transducer 126*c*. The measured gas properties are provided to the controller 130 of the diagnostic system 100 for analysis as part of the diagnostic procedure, as previously described.

In an alternative implementation of the above diagnostic procedure for analyzing functionality of the media beds 118, the oxygen concentrator 102 is configured as shown in FIG. 3B. The diagnostic procedure for the media beds 118 is implemented in accordance with the previous description, except that gas from the gas supply 146 of the diagnostic system 100 enters the oxygen concentrator 102 via the diagnostic inlet port 362*a* and is directed to the subject component 350 (e.g., the media beds 118 in this example) using the diagnostic inlet path 364*a* and the diagnostic inlet valve 366*a*, flows to the media beds 118 where the gas may be separated according to a gas separation cycle (e.g., the PSA cycle or VPSA cycle), and then flows to the diagnostic outlet port 362*b* using the diagnostic outlet path 364*b* and the diagnostic outlet valve 366*b*. In this implementation, the output gas connection 106 may be coupled to the diagnostic outlet port 362*b* to supply the gas output by the media beds 118 to the diagnostic system 100 for analysis, such as by the sensors 136 thereof, as previously described.

In an example of a diagnostic procedure that includes analysis of functionality of the valve assembly 116, the oxygen concentrator 102 is configured as shown in FIG. 3A, and the subject component 350 represents one or more valves from the valve assembly 116. During the diagnostic procedure, for example, in operation 204 of the diagnostic process 200, the diagnostic system 100 sends a command to the oxygen concentrator 102 via the communications connection 104 to cause the first bypass valve 358*a* and/or the second bypass valve 358*b* to move to their respective second positions (e.g., diagnostic positions). This command may be sent in order to bypass the upstream components 352 and/or the downstream components 354, thereby allowing the gas to flow to one or more of the valves from the valve assembly 116 directly, so that operation of the one or more valves may be evaluated in isolation from the upstream components 352 and/or the downstream components 354. As one example, one or more of the valves of the valve assembly 116may be isolated from the compressor 114. As another example, one or more of the valves of the valve assembly 116 may be isolated from the media beds 118. This allows a potential fault of a particular valve from the valve assembly 116 to be diagnosed in isolation from a potential fault of one or more other components of the oxygen concentrator 102.

While isolated from one or more of the other components of the oxygen concentrator 102, gas is supplied to the valve, and the controller 130 outputs commands to change the position of the valve, such as by opening the valve, closing the valve, or sending a signal intended to cause the valve to move to a partially open position corresponding to a particular degree of opening under proportional control. In one implementation, a command from the controller 130 of the diagnostic system 100 is sent to the controller 108 of the oxygen concentrator 102 via the communications connection 104, and the controller 108 issues a command (e.g., a voltage signal or a waveform) to the valve being tested, where the command should cause the valve to move to an intended position. In another alternative, a command from the controller 130 of the diagnostic system 100 is sent directly to the valve being tested via the communications interface without being sent to the controller 108 of the oxygen concentrator 102, and may be sent in a manner that simulates the signal that would be sent by the controller 108 of the oxygen concentrator 102. This implementation further isolates the valve being tested from other components of the oxygen concentrator 102, in that a possible fault of the controller 108 of the oxygen concentrator will not affect diagnosis of the valve being tested in this implementation.

In this implementation, the valve being tested may be isolated from the compressor 114 by supplying gas at a specific pressure (e.g., according to the instructions in the diagnostic procedure) from the gas supply 146 of the diagnostic system 100 via the input gas connection 148. The pressure and/or flow rate downstream from the valve being tested may then be tested using the sensors 124 of the oxygen concentrator 102, or by the sensors 136 of the diagnostic system 100 after transferring the output gas to the diagnostic system using the output gas connection 106, which has the effect of isolating the valve being tested from a potential fault of the sensors 124 of the oxygen concentrator 102. As examples, the pressure downstream of the valve can be tested to check for deviation from an expected value, the flow rate downstream of the valve can be tested to check for deviation from an expected value, and changes in pressure and or flow rate can be monitored while changes in valve position are commanded by the controller 130 of the diagnostic system 100, to determine whether the valve being tested is successfully moving between positions according to the commands being issued.

In an alternative implementation of the above diagnostic procedure for analyzing functionality of one or more of the valves from the valve assembly 116, the oxygen concentrator 102 is configured as shown in FIG. 3B. The diagnostic procedure for the valve is implemented in accordance with the previous description, except that gas from the gas supply 146 of the diagnostic system 100 enters the oxygen concentrator 102 via the diagnostic inlet port 362*a* and is directed to the subject component 350 (e.g., the media beds 118 in this example) using the diagnostic inlet path 364*a* and the diagnostic inlet valve 366*a*, flows to the valve being tested (represented by the subject component 350), and then flows to the diagnostic outlet port 362*b* using the diagnostic outlet path 364*b* and the diagnostic outlet valve 366*b*. In this implementation, the output gas connection 106 may be coupled to the diagnostic outlet port 362*b* to supply the gas output by the valve being tested to the diagnostic system 100 for analysis, such as by the sensors 136 thereof, as previously described.

In an example of a diagnostic procedure that includes analysis of functionality of the sensors 124, the oxygen concentrator 102 is configured as shown in FIG. 3A, and the subject component 350 represents one or more sensors from the sensors 124, such as the flow meter 126*a*, the oxygen sensor 126*b*, and/or the pressure transducer 126*c*. During the diagnostic procedure, for example, in operation 204 of the diagnostic process 200, the diagnostic system 100 sends a command to the oxygen concentrator 102 via the communications connection 104 to cause the first bypass valve 358*a* and/or the second bypass valve 358*b* to move to their respective second positions (e.g., diagnostic positions). This command may be sent in order to bypass the upstream components 352 and/or the downstream components 354, thereby allowing the gas to flow to the sensor being tested directly, so that operation of one or more or the sensors 124 may be tested in isolation from the upstream components 352 and/or the downstream components 354. As one example, one or more of the sensors 124 may be isolated from the compressor 114. As another example, one or more of the sensors 124 may be isolated from the media beds 118. As another example, one or more of the sensors may be isolated from the valve assembly 116. This allows a potential fault of a particular one of the sensors 124 to be diagnosed in isolation from a potential fault of one or more other components of the oxygen concentrator 102.

While isolated from one or more of the other components of the oxygen concentrator 102, an input gas is supplied to the one or more of the sensors 124 that are being tested (e.g., as the subject component). One or more gas properties of the input gas are measured by the sensors 124 and the measurements are transmitted to the controller 130 of the diagnostic system for analysis according to the diagnostic procedure, as previously described. As examples, the flow rate of the input gas may be measured by the flow meter 124*a*, the oxygen concentration of the input gas may be measured by the oxygen sensor 126*b*, and/or the pressure of the input gas may be measured by the pressure transducer 126*c*.

The input gas is provided to the oxygen concentrator 102 from the gas supply 146 using the input gas connection 148, such that the input gas has at least one of a known flow rate, a known oxygen concentration, or a known pressure. In this implementation, the gas supply 146 may be an oxygen concentrator if the oxygen sensor 126*b* is being tested. If the oxygen sensor 126*b* is not being tested, the flow meter 126*a* and the pressure transducer 126*c* may be tested by using a compressor or other source of gas under pressure as the gas supply 146. Supplying the input gas from the gas supply 146 allows testing in isolation from other components of the oxygen concentrator 102, such as the compressor 114 thereof.

To allow comparison of the measurements made by one or more of the sensors 124 of the oxygen concentrator to measurements performed using sensors that are known to be accurate (e.g., by separate testing and/or calibration), measurements of the gas properties of the input gas may be measured by the sensors 136 of the diagnostic system 100 (which may be exposed to the gas produced by the gas supply 146 for this purpose), or the output gas from the oxygen concentrator 102 may be provided to the diagnostic system 100 using the output gas connection 106 for analysis by the sensors 136 of the diagnostic system 100.

In an alternative implementation of the above diagnostic procedure for analyzing functionality of one or more of the sensors 124, the oxygen concentrator 102 is configured as shown in FIG. 3B. The diagnostic procedure for the sensors 124 is implemented in accordance with the previous description, except that gas from the gas supply 146 of the diagnostic system 100 enters the oxygen concentrator 102 via the diagnostic inlet port 362*a* and is directed to the subject component 350 (e.g., the media beds 118 in this example) using the diagnostic inlet path 364*a* and the diagnostic inlet valve 366*a*, flows to the valve being tested (represented by the subject component 350), and then flows to the diagnostic outlet port 362*b* using the diagnostic outlet path 364*b* and the diagnostic outlet valve 366*b*. In this implementation, the output gas connection 106 may be coupled to the diagnostic outlet port 362*b* to supply the gas output by the valve being tested to the diagnostic system 100 for analysis, such as by the sensors 136 thereof, as previously described.

An implementation of the diagnostic system 100 includes the communications interface 112 that is configured for communications with an oxygen concentrator 102. The diagnostic system 100 also includes an output gas interface 134 that is configured for pneumatic communication with the oxygen concentrator 102 in order to receive an output gas from the oxygen concentrator 102. The diagnostic system 100 also includes one or more sensors 136 that are configured to obtain one or more gas property measurements of the output gas that is received from the oxygen concentrator 102 using the output gas interface 134. The diagnostic system 100 also includes the controller 130 that is configured to execute the diagnostic procedure 142. The diagnostic procedure 142 causes the controller 130 to transmit one or more commands to the oxygen concentrator 102 using the communications interface 112, wherein the one or more commands are configured to cause operation of the oxygen concentrator 102. The diagnostic procedure 142 also causes the controller 130 to obtain the one or more gas property measurements from the one or more sensors 136 during operation of the oxygen concentrator 102, and determine the diagnostic result by comparing the one or more gas property measurements obtained from the one or more sensors 136 during operation of the oxygen concentrator 102 to the testing standard described by the diagnostic procedure 142. The diagnostic procedure 142 also causes the controller 130 to output information regarding the diagnostic result for display to the user, for example using a display screen or other display device.

In this implementation of the diagnostic system 100, the one or more commands that are transmitted to the oxygen concentrator 102 by the controller 130 of the diagnostic system 100 may include a command to cause the oxygen concentrator 102 to pneumatically isolate the subject component 350 of the oxygen concentrator 102 relative to one or more other components 352, 354 of the oxygen concentrator 102. The oxygen concentrator 102 may be configured to pneumatically isolate the subject component 350 by operation of one or more valves of the valve assembly 116 of the oxygen concentrator 102.

In this implementation of the diagnostic system 100, the subject component 350 may be the compressor 114 of the oxygen concentrator 102, and the one or more other components 352, 354 of the oxygen concentrator 102 may include one or more of the media beds 118, the valve assembly 116, or the sensors 124. The one or more commands transmitted to the oxygen concentrator 102 using the communications interface 112 may include a command to cause the oxygen concentrator 102 to operate the compressor 114 in a manner intended to achieve at least one of a desired flow rate or a desired pressure of the output gas.

In this implementation of the diagnostic system 100, the subject component 350 may be the media beds 118 of the oxygen concentrator 102, and the one or more other components 352, 354 of the oxygen concentrator 102 may include one or more of the compressor 114, the valve assembly 116, or the sensors 124. The one or more commands transmitted to the oxygen concentrator 102 using the communications interface 112 may include a command to cause the oxygen concentrator 102 to operate in manner intended to achieve at least one of a desired flow rate, a desired oxygen concentration, or a desired pressure of the output gas.

In this implementation of the diagnostic system 100, the subject component 350 may be a valve of the oxygen concentrator 102, and the one or more other components 352, 354 of the oxygen concentrator 102 include one or more of the compressor 114, the media beds 118, or the sensors 124. The one or more commands transmitted to the oxygen concentrator 102 using the communications interface 112 may include a command to the valve to move to an intended position.

In this implementation of the diagnostic system 100, the subject component 350 may be one of the sensors 124 of the oxygen concentrator 102, and the one or more other components 352, 354 of the oxygen concentrator 102 may include one or more of the compressor 114, the media beds 118, or a valve of the valve assembly 116. In some implementations, the controller 130 is configured to obtain one or more gas property measurements from the sensor 124 of the oxygen concentrator 102 for comparison to the one or more gas property measurements from the one or more sensors 124 of the diagnostic system 100.

In this implementation of the diagnostic system 100, the diagnostic system 100 may include an input gas interface 147 that is configured for pneumatic communication with the oxygen concentrator 102, and the gas supply 146 may be configured to supply an input gas to the oxygen concentrator 102 using the input gas interface 147, where the controller 130 is further configured to operate the gas supply 146 to provide the input gas from the gas supply 146 to the oxygen concentrator 102. The gas supply 146 may be operated to provide the input gas to the oxygen concentrator 102 according to at least one of a predetermined pressure or a predetermined flow rate.

In this implementation of the diagnostic system 100, the one or more sensors 136 of the diagnostic system 100 may include at least one of the flow meter 138*a*, an oxygen sensor 138*b*, or the pressure transducer 138*c*. The controller 130 may be further configured to identify information describing the service procedure, such as the service procedure descriptions 144, based on the diagnostic result and the information regarding the diagnostic result includes the information describing the service procedure, such as the service procedure descriptions 144.

Another implementation of the diagnostic system 100 includes the communications interface 112, which is configured for communications with the oxygen concentrator 102. The diagnostic system 100 also includes the input gas interface 147 that is configured for pneumatic communication with the oxygen concentrator 102. The diagnostic system 100 also includes the gas supply 146 that is configured to supply the input gas to the oxygen concentrator 102 using the input gas interface 147. The diagnostic system 100 also includes the controller 130 that is configured to execute the diagnostic procedure 142. The diagnostic procedure 142 causes the controller 130 to transmit one or more commands to the oxygen concentrator 102 using the communications interface 112, supply the input gas to the oxygen concentrator 102, obtain one or more gas property measurements (e.g., from the sensors 136 and/or from the sensors 124) during supply of the input gas to the oxygen concentrator 102, and determine the diagnostic result by comparing the one or more gas property measurements to the testing standard described by the diagnostic procedure 142. The controller 130 is also configured to output information regarding the diagnostic result for display to the user via the user interface 110.

In this implementation of the diagnostic system 100, the input gas may flow through the valve assembly 116 of the oxygen concentrator 102, and the one or more gas property measurements may include at least one of a flow rate, an oxygen concentration, or a pressure measured at a location that is downstream of the valve assembly 116 of the oxygen concentrator 102. Alternatively, the input gas may flow through the media beds 118 of the oxygen concentrator 102, and the one or more gas property measurements may include at least one of a flow rate, an oxygen concentration, or a pressure measured at a location that is downstream of the media beds 118 of the oxygen concentrator 102. Alternatively, the input gas may flow through one of the sensors 124 of the oxygen concentrator 102, and the one or more gas property measurements may include at least one of a flow rate, an oxygen concentration, or a pressure measured by the respective one of the sensors 124 of the oxygen concentrator 102.

In this implementation, the diagnostic system 100 may include the output gas interface 134, which is configured for pneumatic communication with the oxygen concentrator 102 in order to receive the output gas from the oxygen concentrator 102. The diagnostic system 100 may also include one or more of the sensors 136, which are configured to obtain the one or more gas property measurements of the output gas that is received from the oxygen concentrator 102 using the output gas interface 134. Other features that were described previously herein with respect to the diagnostic system 100 and the oxygen concentrator 102 may be included in this implementation.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A diagnostic system, comprising:
- a communications interface that is configured for communications with an oxygen concentrator;
- an output gas interface that is configured for pneumatic communication with the oxygen concentrator in order to receive an output gas from the oxygen concentrator;
- one or more sensors that are configured to obtain one or more gas property measurements of the output gas that is received from the oxygen concentrator using the output gas interface; and
- a controller that is configured to execute a diagnostic procedure, wherein the diagnostic procedure causes the controller to:
  - transmit one or more commands to the oxygen concentrator using the communications interface, wherein the one or more commands are configured to cause operation of the oxygen concentrator, and the one or more commands include a command to cause the oxygen concentrator to pneumatically isolate a subject component of the oxygen concentrator relative to one or more other components of the oxygen concentrator by operation of one or more valves of the oxygen concentrator,
  - obtain the one or more gas property measurements from the one or more sensors during operation of the oxygen concentrator,
  - determine a diagnostic result by comparing the one or more gas property measurements obtained from the one or more sensors during operation of the oxygen concentrator to a testing standard described by the diagnostic procedure, and
  - output information regarding the diagnostic result for display to a user.

2. The diagnostic system of claim 1, wherein the subject component is a compressor of the oxygen concentrator, and the one or more other components of the oxygen concentrator include one or more of a media bed, a valve, or a sensor.

3. The diagnostic system of claim 2, wherein the one or more commands transmitted to the oxygen concentrator using the communications interface include a command to cause the oxygen concentrator to operate the compressor in a manner intended to achieve at least one of a desired flow rate or a desired pressure of the output gas.

4. The diagnostic system of claim 1, wherein the subject component is a media bed of the oxygen concentrator, and the one or more other components of the oxygen concentrator include one or more of a compressor, a valve, or a sensor.

5. The diagnostic system of claim 4, wherein the one or more commands transmitted to the oxygen concentrator using the communications interface include a command to cause the oxygen concentrator to supply gas to the media bed in a manner intended to achieve at least one of a desired flow rate, a desired oxygen concentration, or a desired pressure of the output gas.

6. The diagnostic system of claim 1, wherein the subject component is a valve of the oxygen concentrator, and the one or more other components of the oxygen concentrator include one or more of a compressor, a media bed, or a sensor.

7. The diagnostic system of claim 6, wherein the one or more commands transmitted to the oxygen concentrator using the communications interface include a command to the valve to move to a commanded position.

8. The diagnostic system of claim 1, wherein the subject component is a sensor of the oxygen concentrator, and the one or more other components of the oxygen concentrator include one or more of a compressor, a media bed, or a valve.

9. The diagnostic system of claim 8, wherein the controller is configured to obtain one or more gas property measurements from the sensor of the oxygen concentrator for comparison to the one or more gas property measurements from the one or more sensors of the diagnostic system.

10. The diagnostic system of claim 1, further comprising:
an input gas interface that is configured for pneumatic communication with the oxygen concentrator; and
a gas supply that is configured to supply an input gas to the oxygen concentrator using the input gas interface, wherein the controller is further configured to operate the gas supply to provide the input gas from the gas supply to the oxygen concentrator.

11. The diagnostic system of claim 10, wherein the gas supply is operated to provide the input gas to the oxygen concentrator according to at least one of a predetermined pressure or a predetermined flow rate.

12. The diagnostic system of claim 1, wherein the one or more sensors include at least one of a flow meter, an oxygen sensor, or a pressure transducer.

13. The diagnostic system of claim 1, wherein the controller is further configured to identify information describing a service procedure of the oxygen concentrator based on the diagnostic result and the information regarding the diagnostic result includes the information describing the service procedure.

14. The diagnostic system of claim 1, wherein the oxygen concentrator operates on one of a pressure swing adsorption cycle or a vacuum pressure swing adsorption cycle.

15. A diagnostic system, comprising:
a communications interface that is configured for communications with an oxygen concentrator;
an input gas interface that is configured for pneumatic communication with the oxygen concentrator;
a gas supply that is configured to supply an input gas to the oxygen concentrator using the input gas interface; and
a controller that is configured to operate the gas supply to provide the input gas from the gas supply to the oxygen concentrator and to execute a diagnostic procedure, wherein the diagnostic procedure causes the controller to:
transmit one or more commands to the oxygen concentrator using the communications interface, wherein the one or more commands are configured to cause operation of the oxygen concentrator, and the one or more commands include a command to cause the oxygen concentrator to pneumatically isolate a subject component of the oxygen concentrator relative to one or more other components of the oxygen concentrator by operation of one or more valves of the oxygen concentrator,
supply the input gas to the oxygen concentrator,
obtain one or more gas property measurements during supply of the input gas to the oxygen concentrator,
determine a diagnostic result by comparing the one or more gas property measurements to a testing standard described by the diagnostic procedure, and
output information regarding the diagnostic result for display to a user.

16. The diagnostic system of claim 15, wherein the input gas flows through a valve of the oxygen concentrator, and the one or more gas property measurements include at least one of a flow rate, an oxygen concentration, or a pressure at a location that is downstream of the valve of the oxygen concentrator.

17. The diagnostic system of claim 15, wherein the input gas flows through a media bed of the oxygen concentrator, and the one or more gas property measurements include at least one of a flow rate, an oxygen concentration, or a pressure at a location that is downstream of the media bed of the oxygen concentrator.

18. The diagnostic system of claim 15, wherein the input gas flows through a sensor of the oxygen concentrator, and the one or more gas property measurements include at least one of a flow rate, an oxygen concentration, or a pressure that is measured by the sensor.

19. The diagnostic system of claim 15, further comprising:
an output gas interface that is configured for pneumatic communication with the oxygen concentrator in order to receive an output gas from the oxygen concentrator, wherein the one or more gas property measurements include one or more gas property measurements of the output gas.

20. The diagnostic system of claim 15, wherein the oxygen concentrator operates on one of a pressure swing adsorption cycle or a vacuum pressure swing adsorption cycle.

* * * * *